United States Patent
Sugaya et al.

(10) Patent No.: US 6,713,018 B2
(45) Date of Patent: Mar. 30, 2004

(54) DRY CHEMICAL ANALYSIS ELEMENT CARTRIDGE

(75) Inventors: Fumio Sugaya, Kanagawa-ken (JP); Yoichi Endo, Kanagawa-ken (JP); Nobuaki Tokiwa, Kanagawa-ken (JP); Akihiro Komatsu, Kanagawa-ken (JP); Yoshihiro Seto, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/836,537

(22) Filed: Apr. 18, 2001

(65) Prior Publication Data

US 2002/0000013 A1 Jan. 3, 2002

(30) Foreign Application Priority Data

Apr. 18, 2000 (JP) ........................................ 2000-116262

(51) Int. Cl.[7] .............................................. G01N 31/22
(52) U.S. Cl. ........................... 422/58; 472/99; 472/102; 472/104; 206/215; 206/499; 206/733; 356/244
(58) Field of Search ..................... 422/58, 104, 102; 422/99; 206/733, 215, 499; 356/244

(56) References Cited

U.S. PATENT DOCUMENTS

| | | | | |
|---|---|---|---|---|
| 945,868 A | * | 1/1910 | Sanguinette | 206/733 |
| 985,235 A | * | 2/1911 | Walter | 221/63 |
| 4,187,077 A | * | 2/1980 | Covington et al. | 422/63 |
| 4,190,420 A | * | 2/1980 | Covington et al. | 422/63 |
| 4,417,670 A | * | 11/1983 | Booher | 221/210 |
| 5,080,254 A | * | 1/1992 | Feer | 221/33 |
| 5,363,985 A | * | 11/1994 | Cornell | 221/46 |
| 5,447,690 A | | 9/1995 | Sugaya | 422/64 |
| 5,510,082 A | * | 4/1996 | Arai et al. | 422/64 |
| 5,678,728 A | * | 10/1997 | Leto | 221/185 |
| D424,849 S | * | 5/2000 | Beckwith | D6/512 |
| 2003/0121932 A1 | * | 7/2003 | Wajda | 221/259 |

FOREIGN PATENT DOCUMENTS

JP  5-188058  7/1993 .......... G01N/35/04

* cited by examiner

Primary Examiner—Jill Warden
Assistant Examiner—Sam P. Siefke
(74) Attorney, Agent, or Firm—Sughrue Mion, PLLC

(57) ABSTRACT

A dry chemical analysis element cartridge includes a box-like cartridge casing in which a plurality of chemical analysis elements are stacked and are taken out through an element take-out port formed at one end of the cartridge casing. The inner dimension of the cartridge casing in the direction of the stack of the chemical analysis elements is smaller than the longitudinal and transverse dimensions of each of the chemical analysis elements.

12 Claims, 5 Drawing Sheets

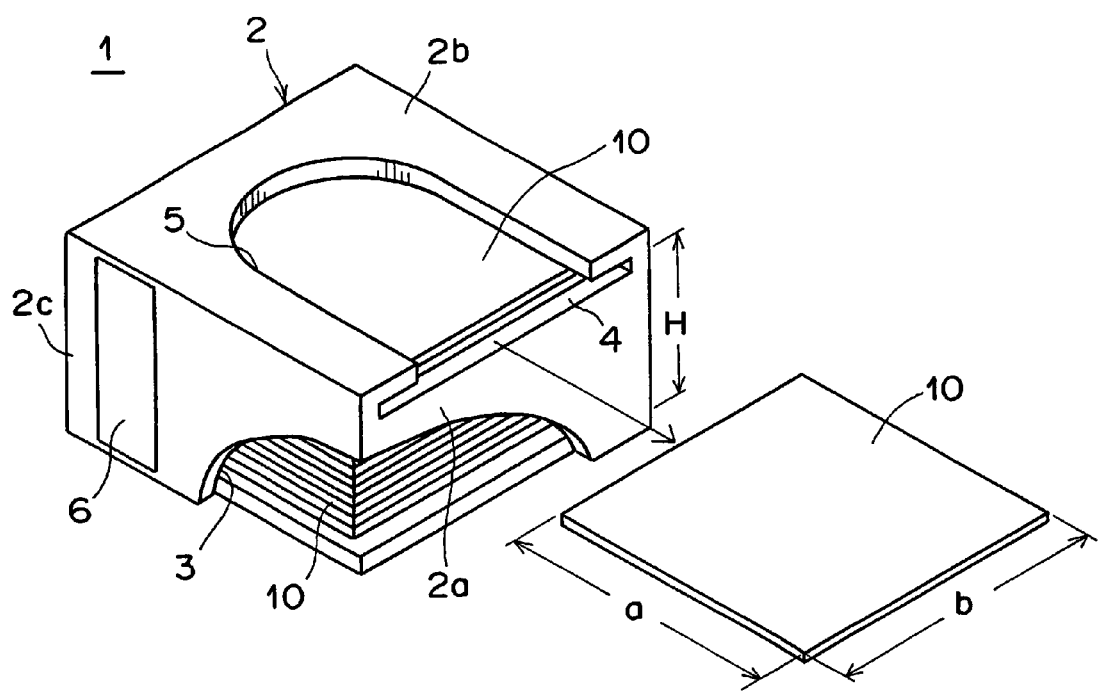
F I G . 1

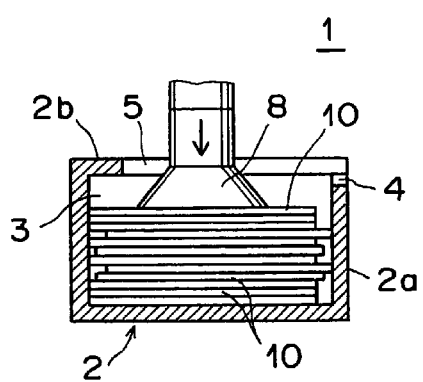 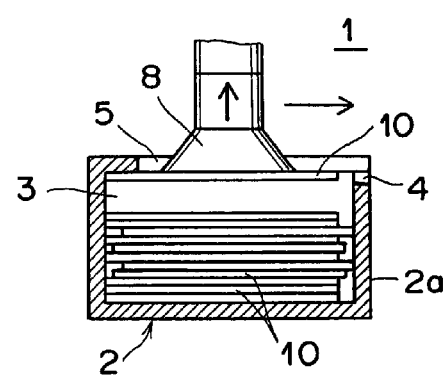
F I G. 3A    F I G. 3B

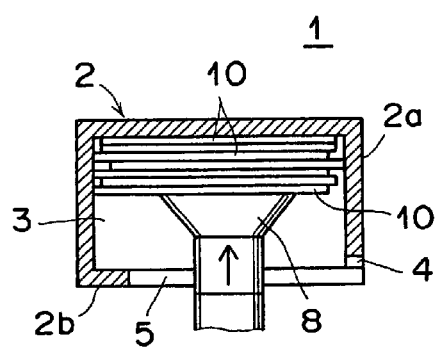
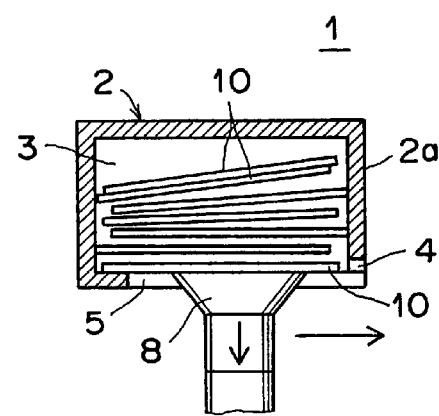
F I G. 4A    F I G. 4B

DRY CHEMICAL ANALYSIS ELEMENT CARTRIDGE

BACKGROUND OF THE INVENTION

1. Field of the Invention

This invention relates to a dry chemical analysis element cartridge for storing and taking out one by one a plurality of dry chemical analysis elements, in the form of a slide with a frame or a film chip without a frame, having a reagent layer which changes in its optical density by chemical reaction, biochemical reaction or immunoreaction with a specific biochemical component contained in a sample such as blood or urine.

2. Description of the Related Art

Recently, there has been put into practice a dry (dry-to-the touch) integrated multi-layered chemical analysis element with which the content of a specific biochemical component contained in a sample liquid, the activity thereof, or the content of solid component in the sample liquid can be quantitatively analyzed by only spotting a droplet of the sample liquid. Further, filter-paper-type test pieces and single or multi-layered test pieces based on improvement of the filter-paper-type test pieces have been developed and partly put into practice.

When quantitatively analyzing the chemical components or the like contained in a sample liquid using such a dry chemical analysis element, a droplet of the sample liquid is spotted on the chemical analysis element (on a spreading layer when the element is provided with the same and directly on there agent layer when the element is not provided with a spreading layer), and the chemical analysis element is held at a constant temperature for a predetermined time in an incubator (incubation) so that a coloring reaction (pigment forming reaction or discoloring reaction of the reagent) occurs, and the optical density of the color formed by the coloring reaction is optically measured. That is, measuring light containing a wavelength which is preselected according to the combination of the component to be analyzed and the reagent contained in the reagent layer is projected onto the chemical analysis element and the optical density of the reagent layer is measured. Then the concentration or the activity of the component to be analyzed is determined on the basis of the optical density according to a calibration curve representing the relation between the concentration of the specific biochemical component and the optical density.

The integrated multi-layered chemical analysis element generally comprises a support sheet of organic polymer and at least one reagent layer formed on the support sheet. Preferably a spreading layer is provided over the reagent layer. The integrated multi-layered chemical analysis element is generally in the form of a film chip of a predetermined shape such as a square or a rectangle. The film chip is sometimes provided with a frame of organic polymer for facilitating automated handling of the chemical analysis element. Further, there has been proposed a technique in which a plurality of the chemical analysis film chips without frame are loaded in a cartridge and the cartridge is loaded in a chemical analysis film supplier of a biochemical analysis apparatus so that the film chips are taken out from the cartridge one by one.

In the dry chemical analysis element cartridge disclosed, for instance, in Japanese Unexamined Patent Publication No. 5(1993)-188058, a plurality of dry chemical analysis elements in the form of a film chip without frame (will be referred to as "frameless chemical analysis element", hereinbelow), while the chemical analysis element with a frame will be referred to as "chemical analysis slide", hereinbelow) are stacked in a cartridge casing, an element take-out port is formed in a side wall of the cartridge casing near to one end face of the casing and connected to an access opening formed in the end face, and a suction pad is brought into contact with one of the frameless chemical analysis elements in the casing through the access opening and laterally moved holding the frameless chemical analysis element under suction force to take out the element through the element take-out port. The stack of the chemical analysis elements are urged toward the access opening by an urging member disposed on the end face opposite to the end face in which the access opening is formed.

Further, there has been known a chemical analysis element cartridge in which a plurality of chemical analysis slides are stacked in a cartridge casing, an element take-out port is formed in a side wall of the cartridge casing near to one end face of the casing, a pressing member is disposed inside the casing to press the stack of the elements from the side remote from the element take-out port and to be movable only toward the element take-out port, the pressing member is moved toward the element take-out port by a plunger to bring the chemical analysis slides to the element take-out port one by one, and the element brought to the element take-out port is ejected through the element take-out port by a pusher blade.

In the chemical analysis element cartridge, a relatively large number of (e.g., 50) chemical analysis elements are stacked in the cartridge casing. When such a large number of elements are loaded in the cartridge, the service life of the chemical analysis elements expires before all the elements in the cartridge are consumed in the case the chemical analysis elements in the cartridge are for a minor measuring item or in the case of a user whose volume of business is relatively small. After the service life expires, the residual chemical analysis elements are generally discarded since after the expiration of the service life, the measuring accuracy deteriorates due to change in the properties of the chemical analysis elements due to, for instance, moisture absorption, which adds to the cost.

Though it is possible to load a relatively small number of chemical analysis elements in a cartridge casing which contains a larger number of chemical analysis elements, this approach is disadvantageous in that even if the number of chemical analysis elements loaded in the cartridge casing is small, a pressing member or an urging member for holding the chemical analysis elements in a stacked state is required, which adds to the cost more as the number of chemical analysis elements to be loaded in the cartridge casing becomes smaller.

SUMMARY OF THE INVENTION

In view of the foregoing observations and description, the primary object of the present invention is to provide a chemical analysis element cartridge in which a relatively small number of chemical analysis elements are contained and can be successfully taken out one by one without using a pressing member or urging member.

In accordance with the present invention, there is provided a dry chemical analysis element cartridge comprising
a box-like cartridge casing in which a plurality of chemical analysis elements are stacked and are taken out through an element take-out port formed at one end of the cartridge casing, wherein the improvement comprises that the inner dimension of the cartridge casing in the direction of stack of the chemical analysis elements is smaller than the longitudinal and transverse dimensions of each of the chemical analysis elements.

A spacer for changing the effective inner dimension of the cartridge casing in the direction of stack of the chemical analysis elements may be provided inside the cartridge casing.

In the dry chemical analysis element cartridge of the present invention, since the inner dimension of the cartridge casing in the direction of stack of the chemical analysis elements is smaller than the longitudinal and transverse dimensions of each of the chemical analysis elements, each chemical analysis element cannot be turned over or erected on one side thereof inside the cartridge casing and can be held in a stacked state without a pressing member or urging member for preventing the chemical analysis element from being turned over. Accordingly, the chemical analysis element cartridge can be manufactured at low cost. Further, since a relatively small number of chemical analysis elements can be loaded in the cartridge, all the chemical analysis elements in the cartridge casing can be consumed before the service life expires even if the chemical analysis elements in the cartridge are for a minor measuring item or the volume of business of the user is relatively small, whereby the residual chemical analysis elements which must be discarded due to expiration of the service life can be lessened and deterioration in measuring accuracy due to change in the properties of the chemical analysis elements can be prevented.

Further, when a spacer for changing the effective inner dimension of the cartridge casing in the direction of stack of the chemical analysis elements is provided inside the cartridge casing, the inner dimension of the cartridge casing in the direction of stack of the chemical analysis elements can be adjusted according to the number of chemical analysis elements loaded in the cartridge casing and/or the thickness of each of the chemical analysis elements loaded in the cartridge casing so that movement of the chemical analysis elements relative to each other during transportation of the chemical analysis element cartridge is prevented and the chemical analysis elements can be prevented from scratching each other.

BRIEF DESCRIPTION OF THE DRAWINGS

FIG. 1 is a perspective view partly cut away of a chemical analysis element cartridge in accordance with an embodiment of the present invention, FIGS. 3A and 3B are views showing a manner of taking out the chemical analysis element from the cartridge casing, FIGS. 4A and 4B are views showing another manner of taking out the chemical analysis element from the cartridge casing.

DESCRIPTION OF THE PREFERRED EMBODIMENT

Figure 2:
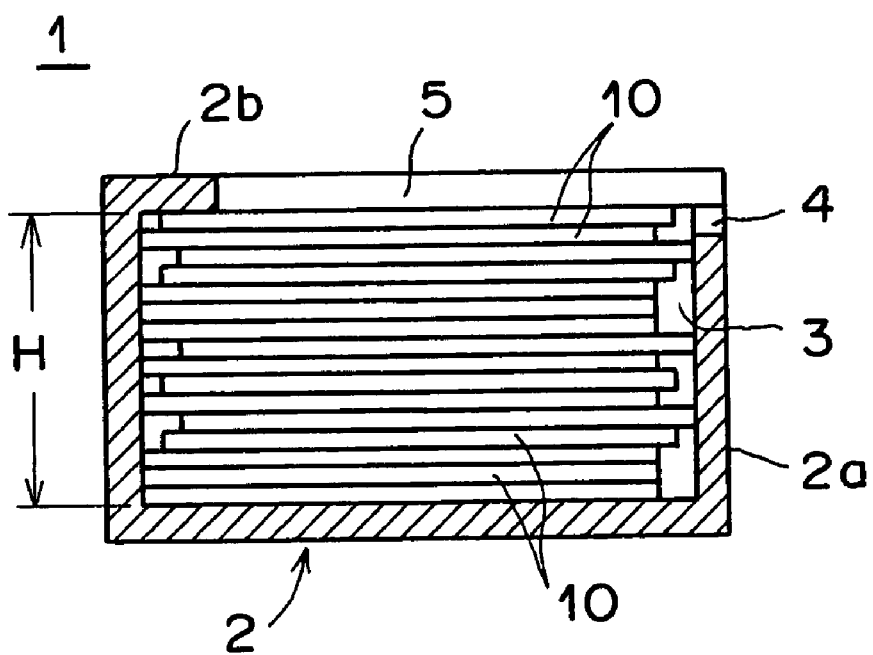
FIG. 2 is a cross-sectional view of the cartridge casing of the cartridge of the embodiment.

In FIGS. 1 and 2, a chemical analysis element cartridge 1 in accordance with an embodiment of the present invention comprises a box-like cartridge casing 2. A plurality of chemical analysis elements 10, each in the form of a square or rectangular film chip without frame, are stacked in the cartridge casing 2. The chemical analysis element 10 comprises a light-transmissive support sheet formed of organic polymer such as polyethylene terephthalate, polystyrene or the like, a reagent layer and a spreading layer. That is, the chemical analysis element 10 is formed by coating or bonding the reagent layer on the support sheet and laminating the spreading layer on the reagent layer. The chemical analysis element 10 is not provided with any frame.

The reagent layer comprises at least one layer composed of a porous layer or a hydrophilic polymer binder such as gelatin containing therein a detecting reagent component which selectively reacts with an analyte and a reagent component (chemical analysis reagent or immunoassay reagent) which is necessary for coloring reaction. The spreading layer is formed of a material resistant to rubbing such as woven or knitted fabric (or cloth) such as polyester or of blend of natural fiber and synthetic fiber, or paper, and functions as a protective layer. Further the spreading layer causes the sample liquid applied thereto to uniformly spread over the reagent layer.

The chemical analysis elements 10 are stacked in the cartridge casings 2 for the respective items of measurement.

The cartridge casing 2 is a tubular member rectangular in cross-sectional shape and is provided with an element holding chamber 3.

The height H (the dimension in the direction of stack of the chemical analysis elements 10) of the element holding chamber 3 is smaller than the longitudinal and transverse dimensions a and b of each of the chemical analysis elements 10 (a>H, b>H). That is, each chemical analysis element 10 cannot be turned over or erected on one side thereof inside the cartridge casing 2 even if there is only one chemical analysis element 10 left in the cartridge casing 2.

The longitudinal and transverse dimensions of the element holding chamber 3 is slightly larger than the longitudinal and transverse dimensions a and b of each of the chemical analysis elements 10, and accordingly, the chemical analysis elements 10 are movable slightly inside the chamber 3 in horizontal directions. However, movement of the chemical analysis elements 10 in the horizontal directions does not adversely affect taking out the chemical analysis elements to be described later.

The cartridge casing 2 is provided with a take-out port 4 in one side wall 2a near to one end face (the top end face in the particular embodiment shown in FIG. 1). The take-out port 4 is in the form of a slit which permits only one chemical analysis element 10 to pass therethrough, and is connected to an access opening 5 formed in the top end face 2b. The access opening 5 is U-shaped and gives access to the uppermost element of the stack of the chemical analysis elements 10 to a suction pad 8 which attracts the uppermost element and holds it under a suction force as will be described later.

The thickness of the chemical analysis elements 10 can differ depending on the analytes to the analyzed and the size of the take-out port 4 in the direction of thickness of the element 10 is set depending upon the thickness of the chemical analysis elements 10 to be loaded in the cartridge casing 2 so that only one chemical analysis element 10 can pass through the take-out port 4 at one time. In the case of the frameless chemical analysis elements 10, the chemical analysis element 10 is curled toward the spreading layer in a dry virgin state, though it is flattened when wet by a sample liquid. Accordingly, the take-out port 4 is formed so that the chemical analysis elements 10 can be taken out one by one even if the elements 10 are curled.

On another side surface 2c of the cartridge casing 2, a display portion 6 is provided and information such as on the properties of the dry chemical analysis elements 10 in the cartridge is displayed on the display portion 6 by magnetic stripes, bar code or the like. Thus, information on the kind of the chemical analysis elements 10, information on the item to be measured, information on the number of chemical analysis elements 10 contained in the cartridge or the like are displayed and a biochemical analyzing system reads the information and carries out biochemical analysis on the basis of the information.

A plurality of dry chemical analysis elements 10 are loaded with their support sheets facing toward the access opening 5. It is preferred that the top end face, the bottom end face or a part of the side walls of the cartridge casing 2 can be removed when the chemical analysis elements 10 are loaded in the cartridge casing 2. The cartridge casing 2 is formed of black plastic such as ABS colored in black or other light-shielding color.

In this particular embodiment, the dry chemical analysis elements 10 are taken out from the cartridge casing 2 in the following manner. FIGS. 3A and 3B show a manner of taking out the chemical analysis elements 10 from above the cartridge casing 2. As shown in FIG. 3A, the cartridge casing 2 is positioned so that the take-out port 4 is held upward and the chemical analysis elements 10 are held on the end face remote from the take-out port 4 under their gravities. In this state, the suction pad 8 is moved above the access opening 5 of the cartridge casing 2 with its sucking face directed downward, and then the suction pad 8 is moved downward under the control of the controller of the biochemical analyzing system. Thus the suction pad 8 is brought into contact with the uppermost chemical analysis element 10 and the suction pad 8 is supplied with suction force from a suction pump (not shown) and attracts the support sheet of the element 10 under the suction force. Since the support sheet is of plastic, the suction force does not leak, and there is no fear of damaging the reagent layer.

Then as shown in FIG. 3B, the suction pad 8 is moved upward to lift the uppermost chemical analysis element 10 to just below the inner surface of the top wall of the cartridge casing 2 and thereafter laterally moved to pass the uppermost chemical analysis element 10 through the take-out port 4, since the take-out port 4 permits only one chemical analysis element 10 to pass therethrough, there is no fear that another chemical analysis element 10 is taken out trailed by the uppermost chemical analysis element 10. Then the chemical analysis element 10 taken out through the take-out port 4 is transferred to a predetermined position in the biochemical analyzing system by the suction pad 8.

FIGS. 4A and 4B show a manner of taking out the chemical analysis elements 10 from above the cartridge casing 2. As shown in FIG. 4A, the cartridge casing 2 is positioned so that the take-out port 4 is held downward and the chemical analysis elements 10 are held on the end face near to the take-out port 4 under their gravities. In this state, the suction pad 8 is moved below the access opening 5 of the cartridge casing 2 with its sucking face directed upward, and then the suction pad 8 is moved upward under the control of the controller of the biochemical analyzing system. Thus the suction pad 8 is brought into contact with the lowermost chemical analysis element 10 and lifts all the chemical analysis elements 10 to press against the inner surface of the top wall of the cartridge casing 2. Then the suction pad 8 is supplied with suction force from a suction pump (not shown) and attracts the support sheet of the lowermost element 10 under the suction force.

Then as shown in FIG. 4B, the suction pad 8 is moved downward to lift the uppermost chemical analysis element 10 to just above the inner surface of the bottom wall of the cartridge casing 2 and thereafter laterally moved to pass the uppermost chemical analysis element 10 through the take-out port 4, since the take-out port 4 permits only one chemical analysis element 10 to pass therethrough, there is no fear that another chemical analysis element 10 is taken out trailed by the uppermost chemical analysis element 10. Then the chemical analysis element 10 taken out through the take-out port 4 is transferred to a predetermined position in the biochemical analyzing system by the suction pad 8.

Figure 5:
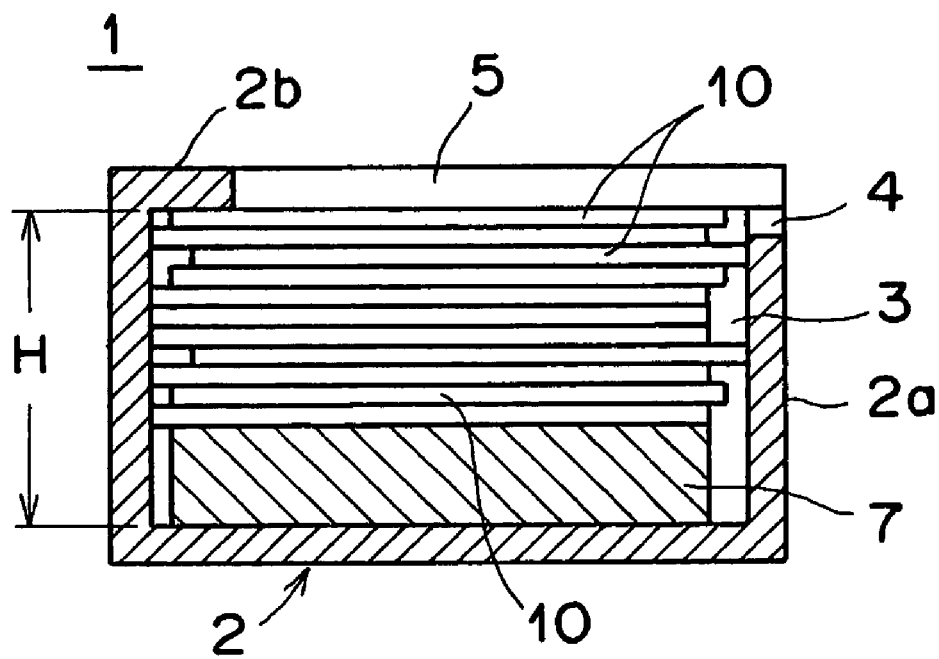
FIG. 5 is a cross-sectional view of the cartridge casing shown in FIG. 2 provided with a spacer.

When the number of chemical analysis elements 10 to be loaded in the cartridge casing 2 is smaller than the capacity of the cartridge casing 2, a spacer 7 may be placed in the cartridge casing 2 and the chemical analysis elements 10 are stacked between the access opening 5 and the spacer 7 as show in FIG. 5.

The height H (the dimension in the direction of stack of the chemical analysis elements 10) of the element holding chamber 3 is smaller than the longitudinal and transverse dimensions a and b of each of the chemical analysis elements 10 (a>H, b>H) as in the cartridge casing shown in FIG. 2. The height H of the element holding chamber 3 may be initially larger than the longitudinal and transverse dimensions a and b of each of the chemical analysis elements 10 (a>H, b>H) so long as the effective height of the element holding chamber 3 is reduced smaller than the longitudinal and transverse dimensions a and b of each of the chemical analysis elements 10 by insertion of the spacer 7.

The spacer 7 may be provided inside the cartridge casing 2 to adjust the inner dimension of the cartridge casing 2 in the direction of stack of the chemical analysis elements 10 according to the number of chemical analysis elements 10 loaded in the cartridge casing 2 and/or the thickness of each of the chemical analysis elements 10 loaded in the cartridge casing 2 so that movement of the chemical analysis elements 10 relative to each other during transportation of the chemical analysis element cartridge 1 is prevented and the chemical analysis elements 10 can be prevented from scratching each other, and so that the chemical analysis elements 10 are prevented from dropping off the cartridge casing 2 when the cartridge casing 2 is vibrated or dropped during transportation or storage.

In place of the frameless chemical analysis element 10, chemical analysis slides maybe loaded in the cartridge casing. In such a case, a pusher blade may be used, in place of the suction pad 8, to push sideways the lowermost chemical analysis slide and ejects it through the take-out port 5.

What is claimed is:

1. A dry chemical analysis element cartridge comprising:
    a box-shaped cartridge casing without a pressing member or urging member for preventing the flat chemical analysis element from being turned over, the cartridge casing comprising:
        an upper inner surface of the cartridge casing being disposed in a parallel relationship to a lower inner surface of the cartridge casing; and
        a first end inner surface of the cartridge casing and a second end inner surface of the cartridge casing being disposed in a perpendicular relationship to the upper inner surface of the cartridge casing and cooperating with the upper inner surface of the cartridge casing and the lower inner surface of the cartridge casing to form an element holding chamber for holding a plurality of flat chemical analysis elements in a planar position that is parallel to the upper inner surface of the cartridge casing;

wherein the plurality of flat chemical analysis elements are stacked in a stack and are taken out one by one through an element take-out port formed at at least one of the first end inner surface of the cartridge casing and the second end inner surface of the cartridge casing, and wherein an inner dimension of the cartridge casing in a direction of the stack of the chemical analysis elements is smaller than a longitudinal dimension and a transverse dimension of each of the chemical analysis elements for preventing the chemical analysis element from being turned over.

2. The chemical analysis element cartridge as defined in claim 1, wherein a spacer for changing the effective inner dimension of the cartridge casing in the direction of the stack of the chemical analysis elements is provided inside the cartridge casing.

3. The chemical analysis element cartridge as defined in claim 1, wherein at least one side surface of said cartridge casing includes a display portion.

4. The chemical analysis element cartridge as defined in claim 2, wherein said effective inner dimension of the cartridge casing in the direction of the stack of the chemical analysis elements is smaller than the longitudinal and transverse dimensions of each of the chemical analysis elements.

5. The chemical analysis element cartridge as defined in claim 2, wherein said spacer is selected to adjust said effective inner dimension of the cartridge casing in the direction of the stack of the chemical analysis elements according to at least one of a number of chemical analysis elements loaded in the cartridge casing and the thickness of each of said chemical analysis elements, whereby movement of said chemical analysis elements relative to each other is prevented.

6. A dry chemical analysis element cartridge comprising:
a box-shaped cartridge casing in which a plurality of flat chemical analysis elements are stacked in a stack and are taken out one by one through an element take-out port formed at a side wall of the cartridge casing;
wherein an inner dimension of the cartridge casing in a direction of the stack of the chemical analysis elements is smaller than a longitudinal and transverse dimension of each of the chemical analysis elements, thereby preventing each of the chemical analysis elements from being turned over inside the cartridge casing and maintaining the chemical analysis elements in a stacked state without using a pressing member or an urging member to press or urge the chemical analysis elements toward an end of the cartridge casing;
wherein the inner dimension of the cartridge casing has a fixed dimension between an inner surface of a top end face of the cartridge casing and an inner surface of a bottom end face of the cartridge casing;
wherein the inner surface of the top end face of the cartridge casing is parallel to the inner surface of the bottom end face of the cartridge casing; and
wherein the inner surface of the top end face of the cartridge casing is perpendicular to the side wall of the cartridge casing.

7. A dry chemical analysis element cartridge comprising:
a box-shaped cartridge casing without a pressing member or urging member for preventing the flat chemical analysis element from being turned over, the cartridge casing comprising:
an upper inner surface of the cartridge casing being disposed in a parallel relationship to a lower inner surface of the cartridge casing; and
a first end inner surface of the cartridge casing and a second end inner surface of the cartridge casing being disposed in a perpendicular relationship to the entire upper inner surface of the cartridge casing and cooperating with the upper inner surface of the cartridge casing and the lower inner surface of the cartridge casing to form an element holding chamber for holding a plurality of chemical analysis elements in a planar position that is parallel to the entire upper inner surface of the cartridge casing;
wherein the plurality of flat chemical analysis elements are stacked in a stack and are taken out one by one through an element take-out port formed at at least one of the first end inner surface of the cartridge casing and the second end inner surface of the cartridge casing, and
wherein an inner dimension of the cartridge casing in a direction of the stack of the chemical analysis elements is smaller than a longitudinal dimension and a transverse dimension of each of the chemical analysis elements for preventing the chemical analysis element from being turned over.

8. The chemical analysis element cartridge as defined in claim 7, wherein a spacer for changing the effective inner dimension of the cartridge casing in the direction of the stack of the chemical analysis elements is provided inside the cartridge casing.

9. The chemical analysis element cartridge as defined in claim 7, wherein at least one side surface of said cartridge casing includes a display portion.

10. The chemical analysis element cartridge as defined in claim 8, wherein said effective inner dimension of the cartridge casing in the direction of the stack of the chemical analysis elements is smaller than the longitudinal and transverse dimensions of each of the chemical analysis elements.

11. The chemical analysis element cartridge as defined in claim 8, wherein said spacer is selected to adjust said effective inner dimension of the cartridge casing in the direction of the stack of the chemical analysis elements according to at least one of a number of chemical analysis elements loaded in the cartridge casing and the thickness of each of said chemical analysis elements, whereby movement of said chemical analysis elements relative to each other is prevented.

12. A dry chemical analysis element cartridge comprising:
a box-shaped cartridge casing in which a plurality of flat chemical analysis elements are stacked in a stack and are taken out one by one through an element take-out port formed at a side wall of the cartridge casing;
wherein an inner dimension of the cartridge casing in a direction of the stack of the chemical analysis elements is smaller than a longitudinal and transverse dimension of each of the chemical analysis elements, thereby preventing each of the chemical analysis elements from being turned over inside the cartridge casing and maintaining the chemical analysis elements in a stacked state without using a pressing member or an urging member to press or urge the chemical analysis elements toward an end of the cartridge casing;
wherein the inner dimension of the cartridge casing has a fixed dimension between an inner surface of a top end face of the cartridge casing and an inner surface of a bottom end face of the cartridge casing;
wherein the inner surface of the top end face of the cartridge casing is parallel to the inner surface of the bottom end face of the cartridge casing; and
wherein the entire inner surface of the top end face of the cartridge casing is perpendicular to each side wall of the cartridge casing.

* * * * *